United States Patent [19]

Ruppender

[11] Patent Number: 4,510,383

[45] Date of Patent: Apr. 9, 1985

[54] DEVICE FOR THE OPTICAL IDENTIFICATION OF A CODING ON A DIAGNOSTIC TEST STRIP

[75] Inventor: Uwe Ruppender, Mannheim, Fed. Rep. of Germany

[73] Assignee: Boehringer Mannheim GmbH, Mannheim, Fed. Rep. of Germany

[21] Appl. No.: 413,293

[22] Filed: Aug. 31, 1982

[30] Foreign Application Priority Data

Sep. 18, 1981 [DE] Fed. Rep. of Germany ....... 3137174

[51] Int. Cl.³ ............................................. G06K 7/10
[52] U.S. Cl. .................................. 235/462; 250/568; 350/114; 382/12; 382/67
[58] Field of Search ............... 235/462, 463, 464, 454; 250/566, 568; 350/114; 382/12, 65, 67

[56] References Cited

U.S. PATENT DOCUMENTS 2,224,646 12/1940 Friedman et al. .............. 235/462 X
3,596,062 7/1971 Street et al. .......................... 235/454
3,894,216 7/1975 Bottles .

Primary Examiner—David L. Trafton
Attorney, Agent, or Firm—Sprung Horn Kramer & Woods

[57] ABSTRACT

A device for the optical identification of a bar coding on a diagnostic test strip in an evaluation device in which the test strip is positively movable relative to a reading device for the coding, with a source of light as a transmitter and a light-sensitive element as a receiver. The bar coding has a high information density and between the test strip and the transmitter and/or between the test strip and the receiver there is, in each case, present a slit aperture and a cylindrical lens. The lens axis runs parallel to the test strip surface carrying the coding and to the code bars, the slit aperture lies in the plane defined by the cylinder axis and the transmitter or receiver and the distance between the lens axis and the test strip surface is substantially such that the focus lines of the lens lie approximately in the test strip surface.

8 Claims, 2 Drawing Figures

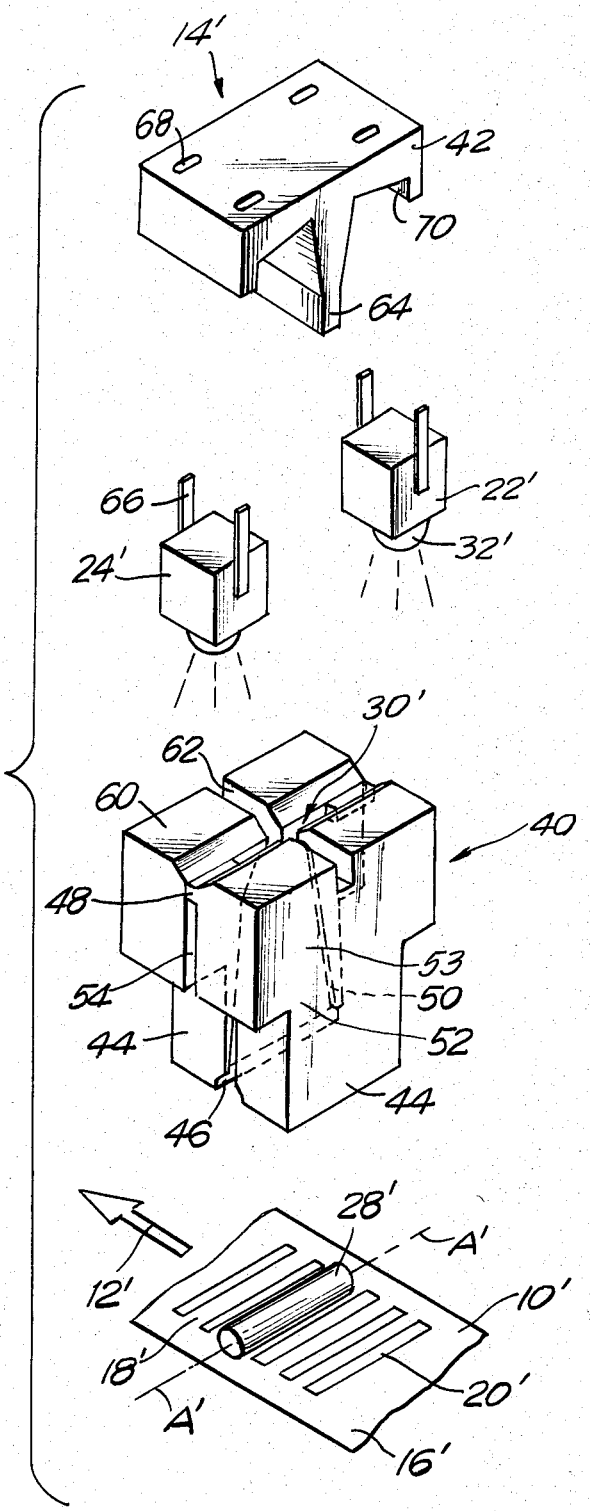

DEVICE FOR THE OPTICAL IDENTIFICATION OF A CODING ON A DIAGNOSTIC TEST STRIP

BACKGROUND OF THE INVENTION

The present invention relates to a device for the optical identification of a coding on a diagnostic test strip in an evaluation device in which the test strip is positively movable relative to a reading device for the coding, with a source of light as a transmitter and a light-sensitive element as a receiver.

A device of this kind is known from U.S. Pat. No. 3,907,503 in which the coding consists of a code block applied to a transparent test strip. In the case of this known device, the coding consists of the distance between this code block and the first adjacent test field of the test strip. For the measurement, the test strip is positively guided between a source of light and a photo-receiver. The light emitted from the source of light is received by the photoreceiver through the test strip. In the case of a uniform movement of the test strip, the time gap between the interruption of the light beam by the code block and by the first test field can be used as a coding for certain information. In the present case, various types of strips differ by the distances between code field and the first test field and by the position of the code field on the test strip.

The known device can certainly be used for reading off very simple information from test strips. However, it would be desirable if more information could be accommodated in the test strip and, for example in the case of the introduction of the test strip into the evaluation device, could be transmitted to its electronic memory.

For the accommodation of a greater amount of information, there is, on the other hand, only a very small space available for the test strip. This leads to a correspondingly high information density with corresponding problems with regard to certainty and lack of disturbance of the transmission.

SUMMARY OF THE INVENTION

Therefore, it is an object of the present invention to provide a simple and economically producible device for the optical identification of a coding on a diagnostic test strip in an evaluation device with positive movement, with which a dependable and low-disturbance transmission of the information stored in the coding is also possible in the case of high information density of the coding.

Thus, according to the present invention, there is provided a device for the optical identification of a bar coding on a diagnostic test strip in an evaluation device in which the test strip is positively movable relative to a reading device for the coding, with a source of light as a transmitter and a light-sensitive element as a receiver, wherein the bar coding has a high information density, between the test strip and the transmitter and/or between the test strip and the receiver there is, in each case, present a slit aperture and a cylindrical lens, the lens axis runs parallel to the test strip surface carrying the coding and to the code bars, the slit aperture lies in the plane defined by the cylinder axis and the transmitter or receiver and the distance between the lens axis and the test strip surface is substantially such that the focus lines of the lens lie approximately in the test strip surface.

The transmitter and the receiver are preferably arranged on the same side of the test strip.

As the bar code, there can be used any such coding which can be applied to a test strip. The bar code consists of a plurality of bars applied parallel to one another, as a rule of differing thickness and at differing distances, on the information carrier. A bar code of high information density is to be understood to be a coding with more than about 10 bits preferably about 20 bits of information per cm.

The cylindrical lens positioned a short distance above the test strip serves for focusing the receiver or transmitter beam of the reading device onto the lines of the bar code. In principle, this could also be achieved with the help of a spherical lens which is otherwise usual for bar code readers. However, for the special conditions in the case of a test strip, this would be less well suited since, in the case of the high information density, such as is necessary for the coding on test strips, a very sharp focusing is necessary due to which even the smallest non-uniformities or errors of the bar code would lead to false reading results. However, such small errors cannot be dependably avoided under the production conditions prevailing in the production of test strips.

Especially preferably, a common cylindrical lens is provided for the receiver and transmitter, the receiver and transmitter being preferably but not necessarily behind a common slit. By means of this arrangement, the advantages provided in any case by the use of a cylindrical lens are even better utilized. The cylindrical lens preferably has the same length as the bar code. The total bar code length is thereby simultaneously imaged on the receiver, i.e. the receiver sees the entirety of the test strip surface lying approximately in the focus line of the cylindrical lens over the whole breadth of the bar code. A combination of great slope steepness, optimal for the conditions in the case of test strips, can thereby be achieved in an ideal manner with simultaneous safety from error in the evaluation.

To a certain extent, these two requirements are counter to one another. Thus, the sharper is the imaging in the case of a bar code reader, the higher is the slope steepness. However, at the same time, the danger increases that small contaminations or errors in the printing of the bar code carrier are falsely indicated as signals and then, for example, lead to false measurement results.

For the conditions prevailing in the case of the usual diagnostic test strips, it must also be possible to dependably identify bar codes with less than 0.2 mm. breadth if it is desired to accommodate thereon a comparatively large amount of information, for example 60 bits. For optical and constructional reasons, known readers cannot achieve the resolution necessary herefor in the case of simultaneously sufficient safety from error.

Preferred embodiments of the present invention are described in more detail, with reference to the accompanying drawings, in which:

BRIEF DESCRIPTION OF THE DRAWINGS

FIG. 2 is a perspective exploded view of a practical embodiment of a device according to the present invention.

DETAILED DESCRIPTION OF THE INVENTION

Figure 1:
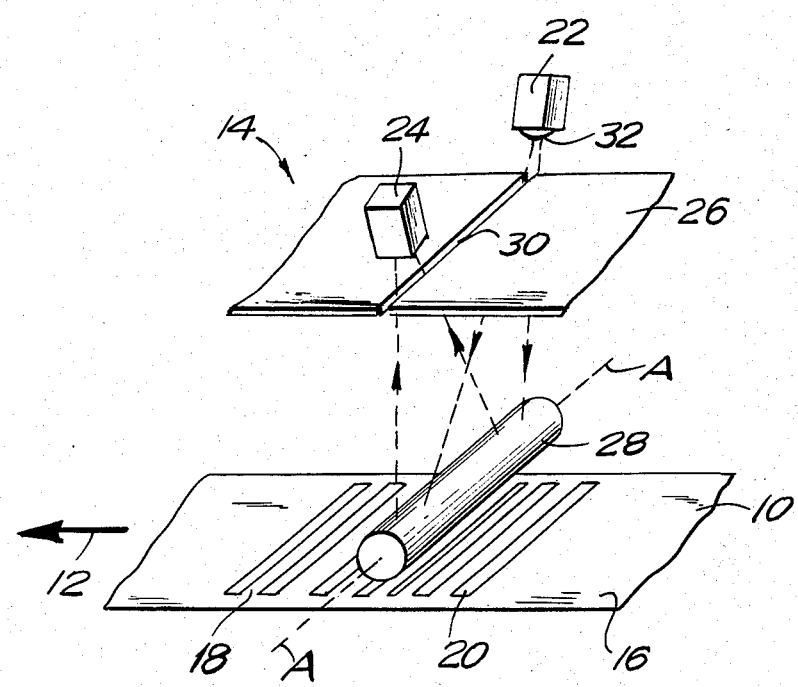
FIG. 1 is a schematic perspective view of the arrangement of the elements necessary for the present invention.

In FIG. 1, there can be seen a part of a test strip 10 which is positively movable in the direction of the arrow 12 under a bar code reader indicated in its totality by the reference 14. The positive guiding thereby provides for a direct movement in the direction of the longitudinal axis of the test strip, the test strip 10 thereby being guided so that the distance between the code reader 14 and the surface of the test strip 16 remains practically constant.

On the surface of the test strip, there is provided a bar coding 18 which consists of individual code bars 20, which vary in their breadth and in their distance apart. The bar codes run parallel to one another and at right angles to the longitudinal direction of the test strip and thus to the direction of movement indicated by the arrow 12.

The code reader 14 comprises a transmitter 22, a receiver 24, a slit aperture 26 and a cylindrical lens 28. The cylindrical lens 28 is, in the illustrated preferred embodiment, constructed as a circular cylinder, the cylindrical axis of which is indicated by the reference A. Between the transmitter 22 and the receiver 24 there is present a light stop (not illustrated) by means of which the action of scattered light from the transmitter 22 on the receiver 24 is avoided. The slot 30 in the slit aperture 26 is illuminated by the transmitter 22. The cylindrical lens 28 provides for an imaging of the illuminated slot 30 on the test strip surface 16. In the illustrated embodiment, the same cylindrical lens 28, the length of which corresponds to about that of the code bar 20, provides for the imaging of the bar code on the receiver 24.

In the illustrated embodiment, the transmitter 22, the receiver 24, the slot 30 and the cylindrical lens 28 are present in a plane which runs at right angles to the test strip surface, an optimum utilization of the intensity of the light transmitter 22 and a substantially distortion-free imaging thereby being achieved.

In the illustrated embodiment, the cylindrical lens 28 is formed as a circular cylinder. Such an embodiment is especially economic to produce and is easy to incorporate. However, other cylindrical cross-sections can also be used for the purpose according to the present invention, for example a semicircle or other lens-shaped cross-section which leads to a concentration of the beams from the transmitter 22 or to the receiver 24. Such shapes often have better imaging properties but, in practice, it has been found that the imaging quality achievable with a circular cylindrical lens is sufficient for the present purpose.

The cylindrical lens 28, formed as a circular cylinder, preferably has a diameter of less than 2 mm. and especially of less than 1 mm. In the case of a circular cylindrical lens, the focal length of the lens is determined by the diameter. Thus, in the case of a small diameter, a small focal length is provided and thus a smaller distance between the cylindrical lens 28 and the test strip surface 16. This is advantageous because a compact construction of the code reader 14 can thereby be achieved.

Furthermore, when using a small cylindrical lens, favorable imaging conditions are provided for practical use. In an especially preferred embodiment, the cylindrical lens has a diameter of 1 mm. and a focal length of 0.75 mm. The distance between the cylinder axis A and the plane of the slit aperture 26 is 8 mm., the slot thereby being 0.2 mm. wide. In the case of these condition, the slot is sharply imaged in a so-called "image plane" below the cylindrical lens, which lies 0.83 mm. below the axis A of the cylindrical lens. Nevertheless, in practice, it has been found that an especially dependable evaluation of the coding is possible when the distance between the cylindrical lens 28 and the test strip surface 16 is slightly smaller, e.g. only 0.7 mm or 0.6 mm. With the distance between the cylindrical lens axis A and the test strip surface 16 shortened to such an extent with regard to the position of the focal plane, a sufficient slope steepness of the signals is achieved in the case of simultaneous substantial freedom from disturbance and minimum contamination of the cylindrical lens. In the case of the dimensions given by way of example, bars of 0.04 mm. breadth can still be identified practically free of error. However, it is important that the test strip surface is, in principle, present at such a distance from the cylindrical lens axis A that the focus line of the cylindrical lens lies substantially in the test strip surface.

In the case of a very great distance between the slot 30 to be imaged and the lens 28, the image plane, in which the slot is sharply imaged, coincides substantially with the focus line of the cylindrical lens. In practice, it has been found that especially good measurement results are achieved when the distance between the slit aperture 26 and the cylindrical lens 28 is at least about ten times as great as the focal length of the lens.

For evaluation of a coding on a diagnostic test strip, the use of infra-red light has proved to be especially useful. For this reason, the source of light used as the transmitter is preferably constructed as an infra-red light emitting diode, whereas the receiver is an infra-red sensitive phototransmitter. Such an embodiment is especially advantageous for battery-operated devices because infra-red light emitting diodes make possible an especially high intensity with only a low current consumption. Furthermore, in the scope of the present invention, it has been found that the usual test strip materials are substantially transparent for infra-red light although in normal light they are non-transparent. If the bar code 20 contain metallic components, such as is preferably the case, then an especially good contrast is obtained between the reflecting bar code 20 and the weakly absorbing material of the test strip 10 in infra-red light. The transmitter 22 and the receiver 24 preferably carry integrated lenses 32 which concentrate the light on the slit.

FIG. 2 illustrates a perspective exploded view of a practical embodiment of the important parts of the device according to the present invention. The parts corresponding to those of FIG. 1 are thereby given the same references provided with a prime. There can be seen the cylindrical lens 28' with its axis A' over a test strip 10', which is provided with a bar coding 18' including bars 20' on surface 16' and is positively guided in the direction of the arrow 12'.

Furthermore, there can be seen the aperture-lens unit 40, the transmitter and receiver holder 42. The parts are illustrated pulled apart in the vertical direction but are present in the apparatus in an assembled state in a vertical shaft for the code reader 14', in which they fit exactly.

The aperture-lens unit 40 consists to two identically shaped formed bodies 44, one of which is shown by unbroken lines, whereas the other one is only indicated by dash-dot lines, in order to make the details of the formed bodies recognizable. On the lower end, a groove 46 can be seen, the shape of which corresponds to that of the cylindrical lens 28'. Above on the formed body 44, there is present a bridge 48 which, as is to be seen from FIG. 2, is only provided on one side of the surface facing the other formed body 44. Since both formed bodies are identical, the opposite-lying formed body has a corresponding bridge 48 which is covered up in the Figure and lies against the corresponding countersurface of the formed body shown by unbroken lines. Between the two bridges, there is present, when the formed bodies 44 lie next to one another, a slot which forms the slit aperture 30'. Under this slot, in FIG. 2 an arcuate recess 50 is to be seen in the region of which the surface 52 encompassed by it is slightly recessed with regard to the front surface 54. In the assembled state, the cylindrical lens 28' is placed in the corresponding groove 46 and the two formed bodies are pressed against one another in the (not illustrated) code reader shaft in such a manner that the bridges 48 lie against the front surfaces 54 of the adjacent formed body 44 and, in the lower region, the cylindrical lens 28' is held by the grooves 46. A gap thereby results between the two formed bodies in the region of the front surfaces 54, which distance corresponds to the height of the bridges 48 and defines the breadth of the illumination slot 30'. In a preferred embodiment, this distance is 0.2 mm. In the region of the recess 50, the recess surface 52 is, for example, backwardly displaced 0.2 mm. so that between the two recessed surfaces there is provided a light shaft 53 of about 0.6 mm. breadth through which the light from the transmitter 22' passes to the cylindrical lens and the reflected light from the cylindrical lens passes to the receiver 24'.

In the surface 60 of the formed bodies 44, there is provided a groove 62 in which a stop member 64 for the transmitter and receiver holder 42 can be placed. By means of this stop member 64, a mutual influencing of transmitter 22' and receiver 24' is prevented. Finally, in FIG. 2 there can also be seen the connecting wires 66 which can be passed through corresponding bores 68 in the transmitter and receiver holder 42 to the appropriate electronic units of the apparatus. The transmitter and receiver holder 42 has recesses 70 to which the transmitter 22' and the receiver 24' are form-lockingly adapted and thus are dependably held when the transmitter and receiver holder 42 is placed in the aperture-lens unit 40 and the code reader 14' resulting therefrom is inserted into an appropriate shaft of the device.

It will be appreciated that the instant specification and examples are set forth by way of illustration and not limitation, and that various modifications and changes may be made without departing from the spirit and scope of the present invention.

What is claimed is:

1. In an evaluation device into which a diagnostic test strip with a high information density bar coding of at least 10 bits per cm on a surface thereof is positively longitudinally movable relative to an optical bar code reader therein having a transmitter comprising light irradiating means and a receiver comprising light-sensitive means, the improvement wherein: the transmitter and the receiver are disposed on the same side of the test strip and wherein the reader comprises a single cylindrical lens disposed between the transmitter and the test strip and the receiver and the test strip with the lens axis running substantially parallel to the test strip surface carrying the coding and to the code bars, means forming a slit aperture between the cylindrical lens and the transmitter and between the cylindrical lens and the receiver, wherein the slit aperture for the transmitter and for the receiver lie in a plane defined by the cylindrical axis of the lens and the transmitter with the distance between the lens axis and the test strip surface being substantially such that the focus lines of the lens lie approximately in the test strip surface.

2. The reader according to claim 1, wherein a common slit aperture and cylindrical lens are provided for the receiver and the transmitter and wherein the cylindrical lens has about the same length as the code bars.

3. The reader according to claim 1, wherein the transmitter, the receiver and the slot aperture lie in a plane at right-angles to the test strip surface.

4. The reader according to claim 1, wherein the cylindrical lens comprises a circular cylinder with a diameter of less than 2 mm.

5. The reader according to claim 4, wherein the lens diameter is at most 1 mm.

6. The reader according to claim 1, wherein the distance between the slit aperture and the cylindrical lens is at least about ten times as great as the focal length of the lens.

7. The reader according to claim 1, wherein the light irradiating means comprises an infra-red light diode and the light sensitive means comprises an infra-red sensitive phototransistor, wherein the diode and phototransistor each comprises an integrated beam-concentrating device.

8. The reader according to claim 1, wherein the slit aperture for the transmitter and for the receiver are the same distance from the lens axis and have the same width.

* * * * *